US006774206B2

(12) United States Patent
Danielmeier et al.

(10) Patent No.: US 6,774,206 B2
(45) Date of Patent: Aug. 10, 2004

(54) POLYASPARTATE RESINS WITH IMPROVED FLEXIBILITY

(75) Inventors: Karsten Danielmeier, Bethel Park, PA (US); Catherine M. Britsch, Pittsburgh, PA (US); Rolf Gertzmann, Leverkusen (DE); Michele E. Vargo, Pittsburgh, PA (US); Terrell D. Wayt, Moundsville, WV (US); Edward P. Squiller, Bridgeville, PA (US)

(73) Assignees: Bayer Polymers LLC, Pittsburgh, PA (US); Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/255,388

(22) Filed: Sep. 26, 2002

(65) Prior Publication Data

US 2004/0063893 A1 Apr. 1, 2004

(51) Int. Cl.[7] .................... C08G 73/00; C08G 63/00; C08G 18/00; C08G 67/00
(52) U.S. Cl. .................... 528/328; 528/44; 528/60; 528/61; 528/64; 528/68; 528/76; 528/272; 528/288; 525/411; 525/419; 525/420
(58) Field of Search ................ 528/44, 60, 61, 528/64, 68, 76, 272, 288, 328, 363, 59, 62, 289; 525/411, 419, 420

(56) References Cited

U.S. PATENT DOCUMENTS

| | | | | |
|---|---|---|---|---|
| 5,126,170 | A | | 6/1992 | Zwiener et al. .......... 427/385.5 |
| 5,236,741 | A | | 8/1993 | Zwiener et al. .......... 427/385.5 |
| 5,466,771 | A | * | 11/1995 | Hicks et al. .................... 528/64 |
| 5,489,704 | A | | 2/1996 | Squiller et al. ................ 560/35 |
| 5,516,873 | A | | 5/1996 | Hick et al. .................... 528/60 |
| 5,561,214 | A | * | 10/1996 | Yeske et al. ................ 528/363 |
| 5,705,602 | A | * | 1/1998 | Kawashima et al. ........ 528/310 |
| 5,714,563 | A | * | 2/1998 | DePompei et al. ............ 528/59 |
| 5,824,424 | A | * | 10/1998 | Haneishi et al. ............. 428/626 |
| 6,013,755 | A | | 1/2000 | Primeaux, II et al. ........ 528/68 |
| 6,399,736 | B1 | | 6/2002 | Primeaux, II et al. ........ 528/84 |
| 6,590,066 | B1 | * | 7/2003 | Roesler ...................... 528/328 |
| 6,605,684 | B2 | | 8/2003 | Primeaux, II et al. ........ 528/68 |

FOREIGN PATENT DOCUMENTS

| WO | WO 01/07399 A1 | * | 2/2001 |
|---|---|---|---|
| WO | 01/07504 | | 2/2001 |

* cited by examiner

Primary Examiner—P. Hampton Hightower
(74) Attorney, Agent, or Firm—Joseph C. Gil; Thomas W. Roy; Gary F. Matz

(57) ABSTRACT

The present invention relates to polyaspartates corresponding to the formula

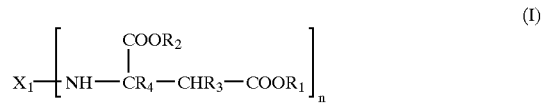

(I)

wherein $X_1$ represents the residue obtained by removing the amino groups from a polyether polyamine having a functionality of n and a number average molecular weight of less than 600, wherein the amino groups are attached to primary carbon atoms and the ether groups are separated by at least two carbon atoms, $R_1$ and $R_2$ are identical or different and represent organic groups which are inert to isocyanate groups at a temperature of 100° C. or less, $R_3$ and $R_4$ are identical or different and represent hydrogen or organic groups which are inert towards isocyanate groups at a temperature of 100° C. or less and n is 2 to 4.

The present invention also relates to polyureas prepared by reacting the polyaspartates and optionally other isocyanate-reactive compounds with polyisocyanates.

20 Claims, No Drawings

POLYASPARTATE RESINS WITH IMPROVED FLEXIBILITY

BACKGROUND OF THE INVENTION

1. Field of the Invention

The present invention relates to polyaspartate resins prepared from low molecular weight polyether polyamines and their use for the production of polyureas having improved flexibility.

2. Description of the Prior Art

Two-component coating compositions containing a polyisocyanate component and a polyaspartate component are known and disclosed in U.S. Pat. Nos. 5,126,170, 5,236,741, 5,489,704 and 5,516,873. The polyaspartates may be used as the only isocyanate-reactive component or they may be blended with polyols, polyamines or blocked polyamines, such as ketimines, aldimines or oxazolidines. The compositions are suitable for the preparation of high quality coatings that are abrasion resistant, solvent resistant and weather resistant.

One of the deficiencies of these polyaspartates is that when reacted with polyisocyanates they do not form flexible coatings, which can be seen from the low elongations of the resulting coatings. One method for improving the flexibility is to prepare the polyaspartates from high molecular weight polyamines, such as Jeffamine D-2000 (available from Huntsman). However, as disclosed in WO 01/07504, the reaction of equimolar amounts of this polyether polyamine with diethyl maleate to form the polyaspartate is only 78% complete after 73 days, and it takes more than 2 years for the reaction to be 100% complete.

Other alternatives for reducing the reaction time are also not feasible. For example, if a large excess of the ester of maleic or fumaric acid is used to reduce the reaction time, then it is necessary to remove the unreacted excess when the reaction is completed, which is a time-consuming, expensive procedure. It is also not feasible to prepared large quantities of the polyaspartates resins in advance because it is extremely difficult to predict customers' needs for the products and because of expensive storage and inventory costs.

Accordingly, it is an object of the present invention to provide polyasparate resins that can be reacted with polyisocyanates to obtain coatings with improved flexibility. It is an additional object of the present invention to provide polyaspartate resins that can be prepared with a short reaction time.

Surprisingly, these objects may be achieved with the polyaspartate resins according to the present invention which are prepared from low molecular weight polyether amines. When reacted with polyisocyanates the resulting coatings possess excellent flexibility. In addition, the polyaspartate resins can be prepared with a relatively short reaction time, which is surprising in view of the prior art that teaches that excessively long reaction times are required to prepare polyaspartates from polyether polyamines.

SUMMARY OF THE INVENTION

The present invention relates to polyaspartates corresponding to the formula

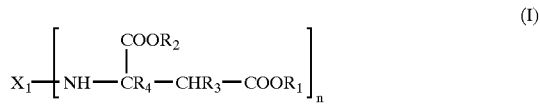

wherein
$X_1$ represents the residue obtained by removing the amino groups from a polyether polyamine having a functionality of n and a number average molecular weight of less than 600, wherein the amino groups are attached to primary carbon atoms and the ether groups are separated by at least two carbon atoms,
$R_1$ and $R_2$ are identical or different and represent organic groups which are inert to isocyanate groups at a temperature of 100° C. or less,
$R_3$ and $R_4$ are identical or different and represent hydrogen or organic groups which are inert towards isocyanate groups at a temperature of 100° C. or less and
n is 2 to 4.

The present invention also relates to polyureas prepared by reacting the polyaspartates and optionally other isocyanate-reactive compounds with polyisocyanates.

DETAILED DESCRIPTION OF THE INVENTION

The polyaspartates according to the present invention correspond to formula I

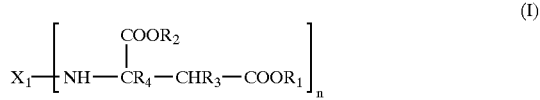

wherein
$X_1$ represents the residue obtained by removing the amino groups from a polyether polyamine having a functionality of n and a number average molecular weight of less than 600, preferably less than 300, wherein the amino groups are attached to primary carbon atoms and the ether groups are separated by at least two carbon atoms,
$R_1$ and $R_2$ are identical or different and represent organic groups which are inert to isocyanate groups at a temperature of 100° C. or less, preferably alkyl groups having 1 to 9 carbon atoms, more preferably alkyl groups having 1 to 4 carbon atoms, such as methyl, ethyl or butyl groups,
$R_3$ and $R_4$ may be identical or different and represent hydrogen or organic groups which are inert towards isocyanate groups at a temperature of 100° C. or less, preferably hydrogen and
n is 2 to 4, preferably 2 or 3 and more preferably 2.

With regard to the preceding definitions $R_1$ and $R_2$ may be different when the polyaspartates are prepared from mixed maleates, such as methylethyl maleate. In addition, one $R_1$ may be different from another $R_1$. For example, when a mixture of maleates, e.g. dimethyl and diethyl maleate, is used to prepare the polyaspartate, one pair of $R_1$ and $R_2$ groups will be methyl and the other will be ethyl.

The polyaspartates may be prepared in known manner as described in U.S. Pat. No. 5,126,170, herein incorporated by reference, by reacting polyether polyamines corresponding to the formula $$X_1\text{—}(\text{—}NH_2)_n \tag{II}$$

with maleic or fumaric acid esters corresponding to the formula $$R_1OOC\text{—}CR_3\text{=}CR_4\text{—}COOR_2 \tag{III}$$

Suitable polyether amines corresponding to formula II are those having linear or branched hydrocarbon chains interrupted by ether groups and having a number average molecular weight of less than 600, preferably less than 300. The amino groups are attached to primary carbons and the ether groups are separated by at least two carbons. Preferably, the backbone of the polyether contains oxypropylene and/or oxyethylene groups.

Preferred polyamines are those corresponding to the formula $$H_2N\text{—}R_6\text{—}O\text{—}R_5\text{—}O\text{—}R_7\text{—}NH_2 \tag{IV}$$

wherein
$R_5$ represents the residue obtained by removing the hydroxyl groups from a linear or branched hydrocarbon radical having 2 to 15 carbon atoms, preferably 2 to 8 carbon atoms and more preferably 2 to 6 carbon atoms, wherein the carbon atoms may optionally be interrupted by ether groups, $R_6$ and $R_7$ may be the same of different and represent linear or branched hydrocarbon radicals containing 2 to 8 carbon atoms, preferably 2 to 6 carbon atoms and more preferably 2 to 4 carbon atoms.

Examples include 2-[2-(2-aminoethoxy)ethoxy] ethylamine (Jeffamine XTJ-504, available from Huntsman), 3-[2-(3-aminopropoxy) ethoxy]propylamine (Etheramine NDPA 10, available from Tomah Products), 3-[3-(3-aminopropoxy)propoxy]propylamine (Etheramine NDPA 11, available from Tomah Products), 3-[4-(3-aminopropoxy) butoxy]propylamine (Etheramine NDPA 12, available from Tomah Products) and 3-{2-[2-(3-aminopropoxy)ethoxy] ethoxy}propylamine (Etheramine DPA-DEG, available from Tomah Products or BASF TTD, available from BASF).

Examples of suitable maleic or fumaric acid esters corresponding to formula III include dimethyl, diethyl and dibutyl (e.g., di-n-butyl), diamyl, di-2-ethylhexyl esters and mixed esters based on mixtures of these and/or other alkyl groups of maleic acid and fumaric acid; and the corresponding maleic or fumaric acid esters substituted by methyl in the 2- and/or 3-position. The dimethyl, diethyl and dibutyl esters of maleic acid are preferred, while the diethyl esters are especially preferred.

The preparation of the polyaspartates takes place by reacting the polyamines with the maleic or fumaric acid esters at a temperature of 0 to 100° C. using the starting materials in such proportions that at least 1, preferably 1, unsaturated group is present for each primary amino group. The reaction may be carried out solvent-free or in the presence of suitable solvents such as methanol, ethanol, propanol, dioxane, aromatic solvents such as toluene and mixtures of such solvents. Preferably, the reaction is carried out solvent-free. The reaction is generally complete within two weeks after the reaction mixture is cooled to room temperature.

It is preferred to add the amine to the flask and then to add the maleic or fumaric acid ester such that the exothermic reaction is controllable. However, it is also possible to add the maleic or fumaric acid ester to the flask and slowly add the amine to the mixture. There is no need to use a catalyst, although one can be added to increase the reaction rate.

Excess starting materials and solvents, especially socyanate-reactive socyanate-reactive solvents, may be removed by distillation after the reaction.

The polyaspartates according to the invention may be combined with polyisocyanates to form two-component compositions that are suitable for the preparation of polyurea coatings, sealants and adhesives. The polyaspartates may also be used as the only isocyanate-reactive component or they may be blended with other isocyanate-reactive components, such as polyols. In accordance with the present invention polyureas include polymers containing urea groups and optionally urethane groups. The polyaspartate mixtures may also be compounds containing amine-reactive groups, such as epoxy groups, carbonate groups and lactones, and reacted to form the corresponding polymers.

Suitable polyisocyanates for preparing the polyureas include monomeric polyisocyanates, polyisocyanate adducts and NCO prepolymers, preferably monomeric polyisocyanates and polyisocyanate adducts. The polyisocyanates have an average functionality of 1.8 to 8, preferably 2 to 6 and more preferably 2 to 5.

Suitable monomeric diisocyanates include those represented by the formula $$R(NCO)_2$$

in which R represents an organic group obtained by removing the isocyanate groups from an organic diisocyanate having a molecular weight of about 112 to 1,000, preferably about 140 to 400. Preferred diisocyanates are those in which R represents a divalent aliphatic hydrocarbon group having 4 to 40, preferably 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α,α',α'-tetramethyl-1,3- and/or -1,4-xylylene diisocyanate, 1-isocyanato-1-methyl-4 (3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof.

Polyisocyanates containing 3 or more isocyanate groups such as 4-isocyanantomethyl-1,8-octamethylene diisocyanate and aromatic polyisocyanates such as 4,4',4"-triphenylmethane triisocyanate and polyphenyl polymethylene polyisocyanates obtained by phosgenating aniline/formaldehyde condensates may also be used.

Preferred organic diisocyanates include 1,6-hexamethylene diisocyanate, 1-isocyanato-3-isocyanatomethyl-3,5,5-trimethylcyclohexane (isophorone diisocyanate or IPDI), bis-(4-isocyanatocyclohexyl)-methane, 1-isocyanato-1-methyl-4(3)-isocyanatomethyl cyclohexane, 2,4- and/or 2,6-toluylene diisocyanate, and 2,4- and/or 4,4'-diphenylmethane diisocyanate.

Suitable polyisocyanate adducts include those prepared from the preceding monomeric polyisocyanates and containing isocyanurate, uretdione, biuret, urethane, allophanate, iminooxadiazine dione, carbodiimide, acylurea and/or oxadiazinetrione groups. The polyisocyanates adducts, which preferably have an NCO content of 5 to 30% by weight, include:

1) Isocyanurate group-containing polyisocyanates which may be prepared as set forth in DE-PS 2,616,416, EP-OS 3,765, EP-OS 10,589, EP-OS 47,452, U.S. Pat. No. 4,288,586 and U.S. Pat. No. 4,324,879. The isocyanato-isocyanurates generally have an average NCO functionality of 3 to 4.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a suitable catalyst, e.g., a trialkyl phosphine catalyst, and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight.

4) rethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342. The allophanate group-containing polyisocyanates have a most preferred NCO content of 12 to 21% by weight.

6) Isocyanurate and allophanate group-containing polyisocyanates which may be prepared in accordance with the processes set forth in U.S. Pat. Nos. 5,124,427, 5,208,334 and 5,235,018, the disclosures of which are herein incorporated by reference, preferably polyisocyanates containing these groups in a ratio of monoisocyanurate groups to mono-allophanate groups of about 10:1 to 1:10, preferably about 5:1 to 1:7.

7) Iminooxadiazine dione and optionally isocyanurate group-containing polyisocyanates which may be prepared in the presence of special fluorine-containing catalysts as described in DE-A 19611849. These polyisocyanates generally have an average NCO functionality of 3 to 3.5 and an NCO content of 5 to 30%, preferably 10 to 25% and most preferably 15 to 25% by weight.

8) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

9) Polyisocyanate containing acylurea groups, which may be prepared by the direct reaction of isocyanates with carboxylic acids or via a carbodiimide intermediate stage as described, e.g., in A. H. M. Schotman et.al. Recl. Trav. Chim. Pay-Basm 1992,111, 88–91, P. Babusiausx et al., Liebigs Ann. Chem. 1976, 487–495, German Auslegeschrift 1 230 778, DE-A 2 436 740 and the literature cited therein.

10) Polyisocyanates containing oxadiazinetrione groups and containing the reaction product of two moles of a diisocyanate and one mole of carbon dioxide.

Preferred polyisocyanate adducts are the polyisocyanates containing isocyanurate, uretdione, biuret, iminooxadiazine dione and/or allophanate groups.

The NCO prepolymers, which may also be used to prepare the polyureas according to the invention are prepared from the previously described monomeric polyisocyanates or polyisocyanate adducts, preferably monomeric diisocyanates, and polyhydroxyl compounds containing at least two hydroxyl groups. These polyhydroxyl compounds include high molecular weight compounds having molecular weights of 500 to about 10,000, preferably 800 to about 8,000, and more preferably 1800 to 8,000, and optionally low molecular weight compounds having molecular weights of less than 500. The molecular weights are number average molecular weights ($M_n$) and are determined by end group analysis (OH number). Products obtained by reacting polyisocyanates exclusively with low molecular weight compounds are polyisocyanates adducts containing urethane groups and are not considered to be NCO prepolymers.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyether polyols, polyester polyols and polycarbonate polyols are preferred. Examples of the high molecular weight and low molecular weight polyhydroxy compounds are disclosed in U.S. Pat. No. 4,701,480, herein incorporated by reference.

These NCO prepolymers preferably have an isocyanate content of 0.3 to 35% by weight, more preferably 0.6 to 25% by weight and most preferably 1.2 to 20% by weight. The NCO prepolymers are produced by reacting the diisocyanates with the polyol component at a temperature of 40 to 120° C., preferably 50 to 100° C., at an NCO/OH equivalent ratio of 1.3:1 to 20:1, preferably 1.4:1 to 10:1. If chain extension via urethane groups is desired during the preparation of the isocyanate prepolymers, an NCO/OH equivalent ratio of 1.3:1 to 2:1 is selected. If chain extension is not desired, an excess of diisocyanate is preferably used, corresponding to an NCO/OH equivalent ratio of 4:1 to 20:1, preferably 5:1 to 10:1. The excess diisocyanate may optionally be removed by thin layer distillation when the reaction is completed. In accordance with the present invention NCO prepolymers also include NCO semi-prepolymers which contain unreacted starting polyisocyanates in addition to the urethane group-containing prepolymers.

Suitable compounds that may optionally be used in combination with the polyaspartates as the isocyanate-reactive component for preparing the two-component compositions include the known isocyanate-reactive compounds from polyurethane or polyurea chemistry. Examples include the high and low molecular weight, polyols previously disclosed for preparing the NCO prepolymers. Also suitable are the known high molecular weight amine-functional compounds, which may be prepared by converting the terminal hydroxy groups of the polyols previously described to amino groups, and the polyaldimines disclosed in U.S. Pat. No. 5,466,771, herein incorporated by reference. The high molecular weight polyols are preferred.

The two-component coating compositions of the present invention may be prepared by mixing the individual components. It is preferred to mix the isocyanate-reactive components together and then to blend the resulting mixture with the polyisocyanate component. The polyisocyanate component and isocyanate-reactive component are present in an amount sufficient to provide an equivalent ratio of isocyanate groups is isocyanate-reactive of 0.5:1 to 2:1, preferably 0.9:1 to 1.5:1, more preferably 0.9:1 to 1.3:1 and most preferably 1:1 to 1.2:1.

Preparation of the compositions may be carried out solvent-free or in the presence of the solvents conventionally used in polyurethane or polyurea chemistry. It is an advantage of the present invention that the quantity of solvent used may be greatly reduced when compared with that required in conventional two-component compositions based on polyisocyanates and polyols.

Examples of suitable solvents include xylene, butyl acetate, methyl isobutyl ketone, methoxypropyl acetate, N-methyl pyrrolidone, Solvesso solvent, petroleum hydrocarbons and mixtures of such solvents.

In the coating compositions to be used for the process according to the invention, the ratio by weight of the total quantity of reactive components to the quantity of solvent is about 40:60 to 100:0, preferably about 60:40 to 100:0.

In addition to the reactive components, the coating compositions may also contain the known additives from coatings technology, such as fillers, pigments, softeners, high-boiling liquids, catalysts, UV stabilizers, anti-oxidants, microbiocides, algicides, dehydrators, thixotropic agents, wetting agents, flow enhancers, matting agents, anti-slip agents, aerators and extenders.

The two-component compositions according to the invention have relatively fast dry times. The resulting polyureas are flexible, have good chemical and weather resistance, and also have a high gloss and good pigmenting qualities.

The reaction to form the urea groups is carried out at a temperature of 10 to 100° C., preferably 20 to 80° C. and more preferably 20 to 50° C. In accordance with the present invention the urea groups initially formed may be converted to hydantoin groups in known manner, e.g., by heating the compounds at elevated temperatures, optionally in the presence of a catalyst. Hydantoin groups will also form over time under ambient conditions. Therefore, the term "urea groups" is also intended to include other compounds containing the group, N—CO—N, such as hydantoin groups.

The invention is further illustrated, but is not intended to be limited by the following examples in which all parts and percentages are by weight unless otherwise specified.

EXAMPLES

Polyaspartate 1—Polyaspartate from 2-[2-(2-aminoethoxy)ethoxy]ethylamine

A round bottom flask was fitted with a stirrer, heating mantle, nitrogen inlet, thermocouple and addition funnel. 74.1 g (1 eq.) of 2-[2-(2aminoethoxy)ethoxy]ethylamine (Jeffamine XTJ-504, available from Huntsman) were admitted to the flask at room temperature. 172 g (1 eq) of diethyl maleate were admitted through the addition funnel over a period of sixty minutes. The temperature of the flask was held at 35° C. The reaction mixture was heated to 60° C., held at that temperature for 12 hours and then cooled to room temperature. An iodometric titration showed that the reaction was >98% complete after one day at room temperature and 100% complete is less than 2 weeks. The clear, colorless final product had an amine number of 227.93 (theoretical amine number: 227.03).

Polyaspartate 2—Polyaspartate from 3-{2-[2-(3-aminopropoxy)ethoxy]ethoxy}propylamine A round bottom flask was fitted with a stirrer, heating mantle, nitrogen inlet, thermocouple and addition funnel. 110.15 g (1 eq.) of 3-{2-[2-(3-aminopropoxy)ethoxy]ethoxy}propylamine (BASF TTD, available from BASF) were admitted to the flask at room temperature. 172 g (1 eq) of diethyl maleate were admitted through the addition funnel over a period of sixty minutes. The temperature of the flask was held at 35° C. The reaction mixture was heated to 60° C., held for 12 hours at that temperature and then cooled to room temperature. An iodometric titration showed that the reaction was >98% complete after one day at room temperature and 100% complete is less than 2 weeks. The clear, colorless final product had an amine number of 196.7 (theoretical amine number: 198.8).

Polyaspartate 3—Polyaspartate from 3-[2-(3-aminopropoxy)ethoxy]propylamine

A round bottom flask was fitted with a stirrer, heating mantle, nitrogen inlet, thermocouple and addition funnel. 91 g (1 eq.) of 3-[2-(3-aminopropoxy)ethoxy]propylamine (Etheramine NDPA 10, Tomah Products) were admitted to the flask at room temperature. 172 g (1 eq) of diethyl maleate were admitted through the addition funnel over a period of sixty minutes. The temperature of the flask was held at 35° C. The reaction mixture was heated to 60° C., held at that temperature for 12 hours and then cooled to room temperature. An iodometric titration showed that the reaction was >98% complete after one day at room temperature and 100% complete is less than 2 weeks. The clear, colorless final product had an amine number of 213 (theoretical amine number: 213).

Polyaspartate 4 (Comparison)—Polyaspartate From a 2000 MW Polyether Diamine

A round bottom flask was fitted with a stirrer, heating mantle, nitrogen inlet, thermocouple and addition funnel. 213.29 g (0.213 eq.) of a polyoxypropylene diamine (Jeffamine D 2000, available from Huntsman) were admitted to the flask at room temperature. 36.71 g (0.213 eq) of diethyl maleate were admitted through the addition funnel over a period of sixty minutes. The temperature of the flask was held at 35° C. The reaction mixture was heated to 60° C., held for 12 hours at that temperature and then cooled to room temperature. An iodometric titration showed that the reaction was not complete after six months at room temperature. The clear, colorless final product had an amine number of 46 (theoretical amine number: 47.8).

Polyaspartate 5

A polyaspartate prepared from bis-(4-aminocyclohexyl)-methane (Desmophen NH 1420, available from Bayer).

Polyaspartate 6

A polyaspartate prepared from 2-methyl-1,5-pentane diamine (Desmophen NH 1220, available from Bayer).

Polyisocyanate 1

An isocyanurate group-containing polyisocyanate prepared from 1,6-hexamethylene diisocyanate and having an isocyanate content of 21.6%, a content of monomeric diisocyanate of <0.2% and a viscosity at 20° C. of 3000 mPa.s (available from Bayer Corporation as Desmodur N 3300).

Application Examples

Polyaspartates 1–6 were hand mixed with polyisocyanate 1 at an NCO:NH equivalent ratio of 1. Viscosity was measured on a Brookfield Viscometer. Pot life is the time from when the two components were mixed until the time when the mixture solidified.

The dry times of films prepared from the compositions were measured by doing a drawdown of the compositions on glass at a 10 mil wet film thickness. At 2-minute intervals, a cotton ball was pressed on the drawdown to test for film cure. The film was completely cured when the cotton ball did not leave an imprint. Tensile strength and % elongation were determined on an Instron 4444 machine according to ASTM D412.

Shore D Hardness was measured by pouring the compositions into aluminum cups (thickness: 0.75 cm) and testing for hardness after curing for 3 days with a Shore Durometer Type D-2, ASTM D2240.

| Example No. | Aspartate | Aspartate rxn time | Dry-time | Pot-life | Shore D hardness | Tensile Strength | % Elongation |
|---|---|---|---|---|---|---|---|
| Example 1 | 1 | <2 weeks | 20 min | 3 min | 20 | 568 | 118 |
| Example 2 | 2 | <2 weeks | 12 min | 2 min | 25 | 795 | 113 |
| Example 3 | 3 | <2 weeks | <2 min | 1 min | 55 | 665 | 107 |
| Comparison Example 4 | 4 | >6 months | >1.5 h | >1.5 h | Shore A 15 | 110 | 40 |
| Comparison Example 5 | 5 | >6 months | 30 min | 20 min | 78 | 7493 | 2.5 |
| Comparison Example 6 | 6 | <2 weeks | <2 min | 1 min | 77 | 8115 | 2 |

Examples 1–3 show clearly improved elongation, which is an indicator for flexibility, versus Comparison Examples 5 and 6, which are based on commercially available polyaspartates. Comparison Example 4 demonstrates that high molecular weight polyether diamines also provide increased flexibility versus Comparison Examples 5 and 6, but the coatings are very soft, the synthesis time is unacceptably long and the flexibility is less than in Examples 1–3. This latter finding must be regarded as surprising since it would be expected that the flexibility would be higher for polyaspartate 4 due to the higher molecular weight of the diamine starting material.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyaspartate composition comprising greater than 98% by weight, based on the weight of the composition, of a polyaspartate corresponding to the formula

(I)

wherein $X_1$ represents the residue obtained by removing the amino groups from a polyether polyamine having a functionality of n and a number average molecular weight of less than 600, wherein the amino groups are attached to primary carbon atoms and the ether groups are separated by at least two carbon atoms, $R_1$ and $R_2$ are identical or different and represent organic groups which are inert to isocyanate groups at a temperature of 100° C. or less, $R_3$ and $R_4$ are identical or different and represent hydrogen or organic groups which are inert towards isocyanate groups at a temperature of 100° C. or less and n is 2 to 4.

2. The polyaspartate of claim 1 wherein $X_1$ represents the residue obtained by removing the amino groups from a polyether polyamine corresponding to the formula

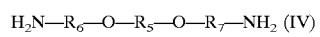

wherein $R_5$ represents the residue obtained by removing the hydroxyl groups from a linear or branched hydrocarbon radical having 2 to 15 carbon atoms, wherein the carbon atoms may optionally be interrupted by ether groups and $R_6$ and $R_7$ may be the same or different and represent linear or branched hydrocarbon radicals containing 2 to 8 carbon atoms.

3. The polyaspartate of claim 2 wherein $R_5$ represents the residue obtained by removing the hydroxyl groups from a linear or branched hydrocarbon radical having 2 to 8 carbon atoms wherein the carbon atoms may optionally be interrupted by ether groups, $R_6$ and $R_7$ may be the same of or different and represent linear or branched hydrocarbon radicals containing 2 to 6 carbon atoms.

4. The polyaspartate of claim 2 wherein $R_5$ represents the residue obtained by removing the hydroxyl groups from a linear or branched hydrocarbon radical having 2 to 6 carbon atoms wherein the carbon atoms may optionally be interrupted by ether groups, $R_6$ and $R_7$ may be the same or different and represent linear or branched hydrocarbon radicals containing 2 to 4 carbon atoms.

5. The polyaspartate of claim 1 wherein $R_1$ and $R_2$ are identical or different and represent alkyl groups having 1 to 9 carbon atoms and $R_3$ and $R_4$ represent hydrogen.

6. The polyaspartate of claim 2 wherein $R_1$ and $R_2$ are identical or different and represent alkyl groups having 1 to 9 carbon atoms and $R_3$ and $R_4$ represent hydrogen.

7. The polyaspartate of claim 3 wherein $R_1$ and $R_2$ are identical or different and represent alkyl groups having 1 to 9 carbon atoms and $R_3$ and $R_4$ represent hydrogen.

8. The polyaspartate of claim 4 wherein $R_1$ and $R_2$ are identical or different and represent alkyl groups having 1 to 9 carbon atoms and $R_3$ and $R_4$ represent hydrogen.

9. The polyaspartate of claim 1 wherein $R_1$ and $R_2$ are identical or different and represent alkyl groups having 1 to 4 carbon atoms, $R_8$ and $R_1$ represent hydrogen and n is 2.

10. The polyaspartate of claim 2 wherein $R_1$ and $R_2$ are identical or different and represent alkyl groups having 1 to 4 carbon atoms, $R_3$ and $R_4$ represent hydrogen and n is 2.

11. The polyaspartate of claim 3 wherein $R_1$ and $R_2$ are identical or different and represent alkyl groups having 1 to 4 carbon atoms, $R_3$ and $R_4$ represent hydrogen and n is 2.

12. The polyaspartate of claim 4 wherein $R_1$ and $R_2$ are identical or different and represent alkyl groups having 1 to 4 carbon atoms, $R_3$ and $R_4$ represent hydrogen and n is 2.

13. The polyaspartate of claim 1 wherein $X_1$ represents the residue obtained by removing the amino groups from 3-[2-(3-aminopropoxy) ethoxy] propylamine.

14. The polyaspartate of claim 5 wherein $X_1$ represents the residue obtained by removing the amino groups from 3-[2-(3-aminopropoxy) ethoxy] propylamine.

15. The polyaspartate of claim 9 wherein $X_1$ represents the residue obtained by removing the amino groups from 3-[2-(3-aminopropoxy) ethoxy] propylamine.

16. The polyaspartate of claim 1 wherein $X_1$ represents the residue obtained by removing the amino groups from 2-[2-(2-aminoethoxy)ethoxy]ethylamine.

17. The polyaspartate of claim 5 wherein $X_1$ represents the residue obtained by removing the amino groups from 2-[2-(2-aminoethoxy)ethoxy]ethylamine.

18. The polyaspartate of claim 9 wherein $X_1$ represents the residue obtained by removing the amino groups from 2-[2-(2-aminoethoxy)ethoxy]ethylamine.

19. A polyurea which comprises the reaction product of a polyisocyanate with an isocyanate-reactive component comprising the polyaspartate of claim 1.

20. The polyurea of claim 19 wherein the isocyanate-reactive component additionally contains a polyol.

* * * * *

UNITED STATES PATENT AND TRADEMARK OFFICE
CERTIFICATE OF CORRECTION

PATENT NO. : 6,774,206 B2  
DATED : August 10, 2004  
INVENTOR(S) : Karsten Danielmeier et al.

It is certified that error appears in the above-identified patent and that said Letters Patent is hereby corrected as shown below:

<u>Column 10,</u>  
Line 14, delete "polyother" and insert -- polyether --.  
Line 32, delete "$R_6$ and $R_7$ may be the same of or different" and insert -- $R_6$ and $R_7$ may be the same or different --.  
Line 64, delete "$R_8$ and $R_1$ represent hydrogen" and insert -- $R_3$ and $R_4$ represent hydrogen --.

Signed and Sealed this

Fourteenth Day of June, 2005

JON W. DUDAS  
*Director of the United States Patent and Trademark Office*